United States Patent [19]
Phillips

[11] Patent Number: 5,728,177
[45] Date of Patent: Mar. 17, 1998

[54] PROSTHESIS WITH FOAM BLOCK ANKLE

[75] Inventor: Van L. Phillips, Rancho Santa Fe, Calif.

[73] Assignee: Flex-Foot, Inc., Aliso Viejo, Calif.

[21] Appl. No.: 692,340

[22] Filed: Aug. 5, 1996

Related U.S. Application Data

[63] Continuation of Ser. No. 290,339, Aug. 15, 1994, abandoned.

[51] Int. Cl.⁶ ..................................................... A61F 2/66
[52] U.S. Cl. .............................. 623/55; 623/49; 623/53
[58] Field of Search ............................................ 623/47–56

[56] References Cited

U.S. PATENT DOCUMENTS

| | | |
|---|---|---|
| 25,238 | 8/1859 | Bly . |
| 56,983 | 8/1866 | Nicholas . |
| 619,731 | 2/1899 | Doerflinger et al. . |
| 809,876 | 1/1906 | Wilkins . |
| 817,340 | 4/1906 | Rosenkranz . |
| 2,315,795 | 4/1943 | Johnson et al. . |
| 2,594,945 | 4/1952 | Lucas et al. . |
| 2,692,392 | 10/1954 | Bennington et al. . |
| 3,784,988 | 1/1974 | Trumpler . |
| 3,833,941 | 9/1974 | Wagner . |
| 3,874,004 | 4/1975 | May .............................. 623/50 |
| 3,982,280 | 9/1976 | Asbelle et al. . |
| 4,360,931 | 11/1982 | Hampton . |
| 4,892,554 | 1/1990 | Robinson . |
| 5,019,109 | 5/1991 | Voisin . |
| 5,030,239 | 7/1991 | Copes .............................. 623/52 |
| 5,062,859 | 11/1991 | Naeder . |
| 5,085,665 | 2/1992 | Radocy et al. .............................. 623/55 |
| 5,112,356 | 5/1992 | Harris et al. . |
| 5,156,632 | 10/1992 | Wellershaus .............................. 623/55 |
| 5,181,932 | 1/1993 | Phillips . |
| 5,258,039 | 11/1993 | Goh et al. . |
| 5,376,140 | 12/1994 | Ryan .............................. 623/53 |

FOREIGN PATENT DOCUMENTS

| | | |
|---|---|---|
| 1371996 | 10/1994 | European Pat. Off. . |
| 2640499 | 6/1990 | France . |
| 621576 | 4/1949 | United Kingdom . |

*Primary Examiner*—John G. Weiss
*Assistant Examiner*—Bruce E. Snow
*Attorney, Agent, or Firm*—Knobbe, Martens, Olson & Bear, LLP

[57] ABSTRACT

A foam block ankle prosthesis for Symes amputees that has a lower foot plate and an upper ankle plate connected by a monolithic foam block. The foot plate is generally sized the same as a surrounding cosmesis, while the ankle plate is substantially shorter, with the foam block forming a resilient ankle region underneath the ankle plate. The plates are bonded to the foam block with suitable adhesive. An attachment member is fastened to an upper surface of the ankle member slightly rearward from its centerline and approximately located where a centerline of the wearer's ankle would be. During a walking stride the wearer experiences a smooth rollover or transition of compressive forces from a heel-strike position to a toe-off position.

20 Claims, 2 Drawing Sheets

5,728,177

PROSTHESIS WITH FOAM BLOCK ANKLE

This application is a continuation of U.S. patent application Ser. No. 08/290,339, filed Aug. 15, 1994 now abandoned.

FIELD OF THE INVENTION

The present invention pertains to prosthetic feet and, more particularly, to a simply constructed, low-profile prosthetic foot having enhanced dynamic performance characteristics.

BACKGROUND OF THE INVENTION

In the prosthetics market, the conventional SACH foot has been the most widely prescribed artificial foot over the past 35 years. The SACH foot generally includes a solid ankle and cushioned heel foot mounted to a limb along an approximate hinge axis taken through the ankle. The SACH foot has been popular precisely for its simplicity, and thus economy, but includes certain drawbacks in terms of dynamic response characteristics. Specifically, the low end SACH feet do not provide much energy storage and release, as do more sophisticated prosthetic feet.

Some patients undergo what is known in the art as a Symes amputation, where the foot is severed from the leg near the ankle region. Because the Symes patient's calf and shin function as the stump for prosthetic purposes, prosthetic devices utilized by the patient must either be relatively compact, so as to be attachable below the point of amputation, or must be configured to accommodate the patient's shin and calf while attached thereto or higher up on the wearer's leg. Prior art prostheses available to Symes patients typically include an artificial foot bonded or bolted onto the bottom end of a socket worn on a patient's stump. These compact prosthetic feet can also attach below a downwardly depending pylon secured to a socket higher up on the amputee's leg. For such compact prostheses, it is difficult to provide the level of dynamic response approximating the original ankle and foot due to the lack of vertical space available. Some attempts at providing the appropriate response characteristics of the original ankle and foot in Symes foot prosthesis involve the use of rubber cushions, or bumpers, between a lower leg and the foot. Many of these require a pivotable bolt attachment between the leg and the foot. Unfortunately, many of these rubber cushion devices have limited durability due to the difficulty in bonding the rubber portions to the solid leg or foot portions, or are relatively complex, requiring several machined parts, which adds to the cost.

Consequently, there is a need for an inexpensive and durable Symes foot prosthesis with improved performance characteristics.

SUMMARY OF THE INVENTION

In response to problems with the prior art, the present invention provides a simple, inexpensive prosthetic foot having a foot element, an ankle element, and an ankle block of compressable material positioned between and connected to the foot element and ankle element. Preferably, the foot element has a length roughly equal to the length of a human foot, while the ankle element is somewhat shorter. This foot element is constructed of a resilient material capable of flexing along its length. The prosthetic foot further has an attachment member connected to the ankle element opposite the ankle block for coupling the foot to a downwardly depending leg. In the preferred embodiment, the ankle element is also capable of flexing along its length. Further, the ankle block is sized roughly the same length as the ankle element, and both the ankle block and ankle element extend roughly one-third the length of the foot element.

In the preferred embodiment, the foot element and the ankle element both comprise plates. In addition, the ankle block preferably comprises a monolithic element constructed of foam. Also, desirably, the foot plate and the ankle plate have widths roughly equal to that of a wearer's amputated foot.

In another form, the present invention provides a basic prosthetic foot having enhanced performance characteristics generally comprising a lower foot plate, an upper ankle plate, and a monolithic foam ankle block joining the two plates. Both the foot plate and the ankle plate are constructed of strong, flexible material, preferably fiberglass. The foot plate is sized approximately equal to a human foot being replaced, while the ankle plate has a similar width but has a shorter length than the foot plate. The ankle block has a length and width approximately equal to the ankle plate and is aligned therewith, both being positioned rearward of a centerline of the foot plate. An attachment stud extends upward from the ankle plate to mount an attachment member or other coupling member for mating with a stump of the wearer. During a walking stride, the combination of the foam block ankle and flexible plates provides a smooth rollover from a heel-strike to a toe-off position.

In accordance with a preferred embodiment of the present invention, the foam block ankle is constructed of a polyurethane foam having a thickness of approximately two inches. The attachment stud is positioned to the rear of the center of the ankle plate to simulate the precise line of force through an actual ankle. During a walking stride, the majority of the compressive forces imparted by the wearer is absorbed by the foam block ankle, with a small portion being absorbed by the flexible plates themselves. The foam block is preferably a high density cellular polyurethane foam.

DESCRIPTION OF THE PREFERRED EMBODIMENTS

Figure 1:
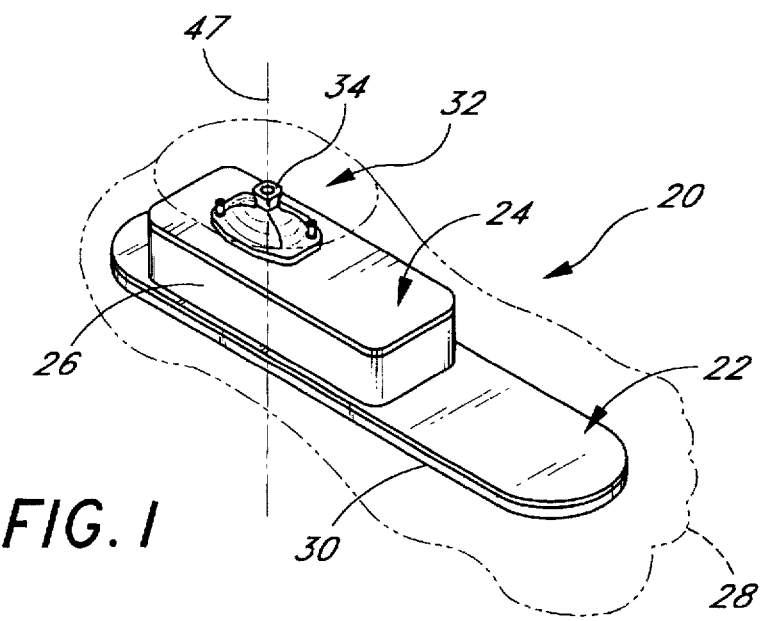
FIG. 1 is a perspective view of a preferred prosthetic foot of the present invention within an outer foot cosmesis shown in phantom.
Figure 2:
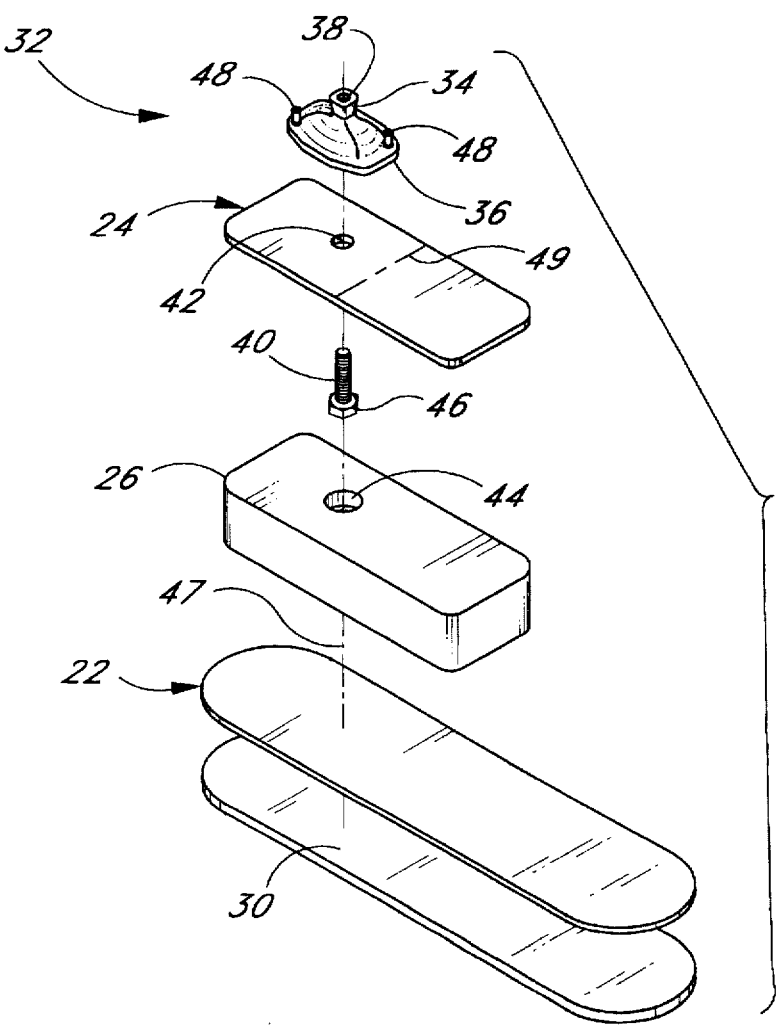
FIG. 2 is a perspective exploded view of the prosthetic foot of FIG. 1.

Now with reference to FIGS. 1 and 2, a prosthetic foot 20 of the present invention is shown in assembled and exploded perspective views, respectively. The prosthetic foot 20 generally comprises a lower foot plate 22, an upper, smaller ankle plate 24, and a layer or block of resilient foam material 26 connecting the foot plate to the ankle plate. The foot plate 22 has a length and width roughly equal to the approximate length and width of the particular wearer's amputated foot and is sized to fit within an outer flexible cosmesis 28, shown in phantom. The ankle plate 24 and foam block 26 have approximately the same horizontal cross-sectional size. The ankle plate 24 and foam block 26 are centered transversely with respect to and are generally positioned over the back half of the foot plate 22. The foam block 26 is sandwiched between the foot plate 22 and ankle plate 24, and is preferably bonded to both plates. The foot plate 22 may also have a lower sole cushion 30 providing protection for the inner surfaces of the cosmesis 28 from the corners of the foot plate.

The prosthetic foot 20 is connected to a stump or lower leg pylon (not shown) of a wearer via an attachment member 32. The attachment member 32 is adapted to be fastened to an upper surface of the ankle plate 24 and includes a coupling knob 34 for mating with a coupling member on the pylon. In the illustrated embodiment, the attachment member 32 comprises a base plate 36, having the upstanding coupling knob 34 formed integrally therewith. The attachment member further may include a pair of upstanding location pins 48, which help transmit torsional forces between the pylon and the foot prosthesis 20.

A central threaded bore 38 in the knob 34 receives a fastening bolt 40 extending upwardly through an aperture 42 in the foot plate 24. The foam block 26 is preferably formed with a cavity 44 in its upper surface to receive the downwardly protruding bolt head 46. Other attachment members, as may be apparent to those of skill in the art, can be attached via the upwardly directed fastening bolt 40. The center of the bolt 40 defines an attachment axis 47 which is generally aligned with the vertical centerline of an imaginary ankle so as to more faithfully simulate the location at which forces are transmitted between leg and foot. This centerline is positioned rearwardly from the longitudinal center of the ankle plate 24 and foam block 26 and, preferably, approximately two-thirds of the way from the front end of the ankle plate 24 and ankle block 26. Thus, there is substantially more foam block material forward of the centerline 47, as well as the attachment member 32, than to the rear.

Both the foot plate 22 and the ankle plate 24 are preferably constructed of fiberglass, which provides strength and flexibility. Alternatively, the plates 22 and 24 may be formed by a plurality of lamina embedded in a hardened, flexible polymer. In other arrangements the plates 22 and 24 may be formed of other materials, such as carbon fibers, as may be apparent to one skilled in the art. The desirable properties of the plates 22, 24 are that they are relatively resilient so as to withstand cracking upon application of repeated bending stresses, yet have sufficient flexibility to enhance the performance characteristics felt by the wearer, in conjunction with the properties of the foam block 26.

Figure 3A:
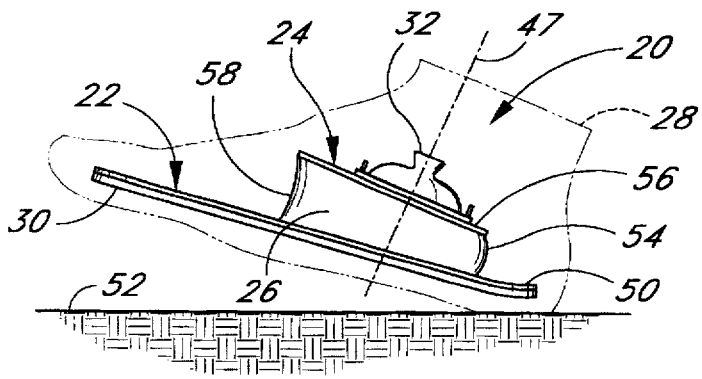
FIG. 3a is an elevational view of the prosthetic foot in a heel-strike position of a walking stride.
Figure 3B:
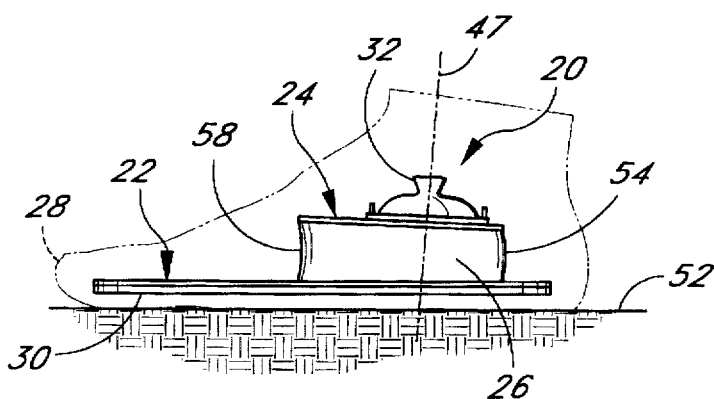
FIG. 3b is an elevational view of the prosthetic foot in a flat position of a walking stride.
Figure 3C:
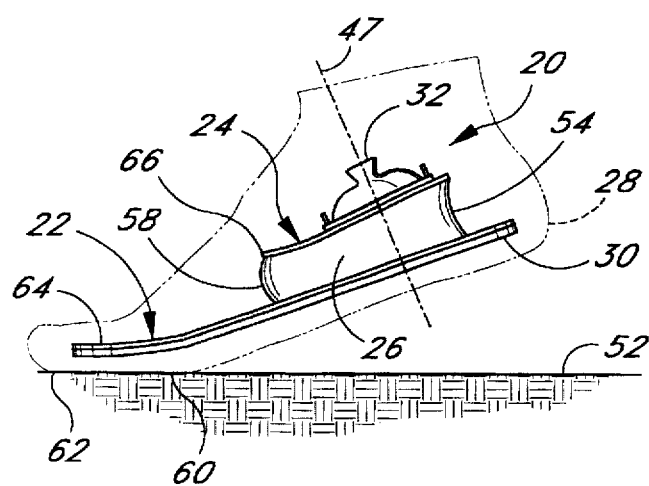
FIG. 3c is an elevational view of the prosthetic foot in a heel-off position of a walking stride.
Figure 3D:
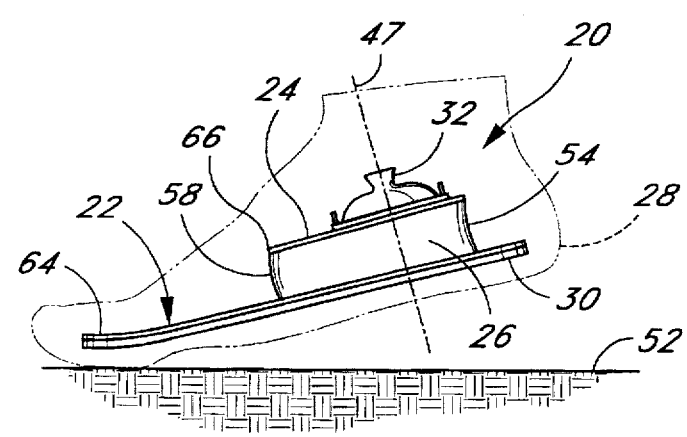
FIG. 3d is an elevational view of the prosthetic foot in a toe-off position of a walking stride.

To more fully explain the improved performance characteristics of the present prosthetic foot 20, FIGS. 3a–3d show "snapshots" of a prosthetic foot in several positions of a walking stride. More particularly, FIG. 3a shows a heel-strike position, FIG. 3b shows a generally flat position, FIG. 3c shows a heel-off position, and FIG. 3d shows a toe-off position. Throughout the various positions shown for a walking stride, the present prosthetic foot 20 provides a smooth and generally life-like response to the wearer. During a walking stride, the foam block 26 transmits the forces imparted thereon by the foot plate 22 and ankle plate 24, and experiences a gradual rollover, or migration of the compressed region, from rear to front.

With specific reference to FIG. 3a, a first position of a walking stride generally entails a heel strike, wherein the wearer transfers all of his or her weight to the heel of the leading foot. In this case, a rear portion 50 of the foot plate 22 comes in contact with a ground surface 52, albeit through the sole cushion 30 and cosmesis 28. The flexible nature of the foot plate 22 allows it to bend slightly in the rear portion 50, but most of the compressive stresses from the weight of the wearer through the prosthetic foot 20 to the foot plate 22 are absorbed by a rear region 54 of the foam block 26. Further, a slight amount of bending may occur in a rear region 56 of the ankle plate 24, although this bending is limited by the short lever arm between the axis of attachment 47 and effective center of application of resisting force by the walking surface on the foot 20. Additionally, the foam block 26 reinforces all but a small portion of the rear portion 50 of the foot portion against bending. A front portion 58 of the foam block 26 experiences a stretching, or tension, due to the attachment along the entire lower edge of the foam block with the foot plate 22.

Next, in FIG. 3b, the wearer reaches a generally flat-footed position, whereby the foot plate 22 contacts the ground 52 along substantially its entire length, again through the sole cushion 30 and cosmesis 28. In this position the weight of the wearer is directed substantially downwardly, so that the compression along the length of the foam block 26 is only slightly greater in the rear portion 54 due to the off-center application of force. Although this view freezes the compressive stress distribution as such, in reality the weight of the wearer is continually shifting from behind the centerline 47 of the attachment member 32 to forward thereof. Thus, as the wearer continues through the stride, the compression of the foam block 26 travels from the rear portion 54 toward the front portion 58. This migration of the compressed region can be termed "rollover."

In a next snapshot of the walking stride, FIG. 3c shows the prosthetic foot 20 in a "heel-off" position. This is the instant when the wearer is pushing off using ball 60 and toe 62 regions of the foot. Thus, a large compressive force is generated in the front region 58 of the foam block 26, causing the rear region 54 to experience a large amount of separation or tension. The front tip 64 of the foot plate 22 may bend substantially to absorb some of the compressive stresses. Likewise, the front tip 66 of the ankle plate 24 may bend somewhat at this point. It is important to note that although the foam block 26 absorbs a majority of the compression generated by the wearer, the foot plate 64 and ankle plate 66 are designed to work in conjunction with the foam block and provide enhanced dynamic performance. Further, the flexing of the foot plate 64 and ankle plate 66 relieves some of the extreme sheer stresses applied to the interfaces between the foam block 26 and plates, thus increasing the life of the bonds formed therebetween.

In FIG. 3d, a final position of the walking stride is shown, wherein the prosthetic foot 20 remains in contact with the ground 52, but some of the weight of the wearer is being transferred to the opposite foot, which has now moved forward. In this position, there is less bending of the front tip 64 of the foot plate 22 and less compression of the front portion 58 of the foam block 26. Likewise, the front tip 66 of the ankle plate 24 may flex a slight amount, depending on the material and thickness utilized. The region of highest compression of the foam block 26 remains at the farthest forward region 58, but it is reduced from the compression level of the heel-off position of FIG. 3c. Thus, the rear portion 54 of the foam block 26 experiences a small amount of tension or spreading.

Although the foot plate 22 is shown as substantially flat in the illustrations, it may be constructed with a slight arch in the center region, with the toe and heel regions being slightly upwardly curved to simulate the natural curve of the sole of the foot. However, even with a flat foot plate 22 used to reduce the cost of the final product, the foot 20 still performs substantially better than other SACH feet.

The foam block 26 is preferably constructed of a relatively dense cellular polyurethane foam, and more preferably is a polyurethane foam having a density in the range of 25–35 lbs/ft$^3$, with a preferred density of 30 lbs/ft$^3$. The cellular foam provides sufficient springiness for a natural feeling stride with some spring response without the drawback of limited compression associated with solid elastomeric bumpers. Furthermore, the cellular nature of the block 26 makes it lighter than solid elastomers.

The foam block 26 may be provided in varying heights or thicknesses but is most effective with a thickness of between one and three inches, and more preferably the foam block has a thickness of approximately two inches. The foam block 26 thus provides a relatively stiff yet flexible ankle region, which can be customized for various wearers. More specifically, heavier wearers may need a denser urethane foam for the foam block 26, while lighter wearers may require a less dense foam or less thickness.

The illustrations of FIGS. 3a–3d show a typical sequence of compression of the foam block 26 during a walking stride. However, although not illustrated, the foam block 26 also provides enhanced performance for the wearer in inversion or eversion. Prior SACH feet were often relegated to pivoting about a horizontal axis through the ankle and had relatively little flexibility from side to side. The present foam block 26 allows the wearer to walk transversely up sloped surfaces, for example, with the foot plate conforming to the terrain while the ankle plate can remain relatively horizontal due to the sideways compression of the ankle block 26. Again, as the wearer lifts his or her foot, the foam block ankle 26 resumes its original shape, thus helping the wearer as energy is stored and then released.

It can now be appreciated that the "feel" of the present prosthetic foot 24 is greatly enhanced by the cooperation between the foot plate 22, ankle plate 24, and foam block 26. As the wearer continues through the walking stride, the dynamic response from the prosthetic foot 20 is smooth as the foam block 26 compresses in different regions. Further, the flexing of the plates 22, 24 assists in smoothly transmitting the various bumps and jars found in uneven walking surfaces.

Although this invention has been described in terms of certain preferred embodiments, other embodiments that are apparent to those of ordinary skill in the art are also within the scope of this invention. Accordingly, the scope of the invention is intended to be defined by the claims that follow.

It is claimed:

1. A prosthetic foot, comprising:
   a monolithic foot plate having toe and heel portions and a length from toe to heel roughly equal to that of a natural human foot being replaced, said foot plate comprising a resilient multi-laminate material capable of flexing substantially along its length;
   an ankle plate having a length substantially shorter than said foot plate, said ankle plate being disposed substantially above and roughly parallel to said foot plate so as to define a space therebetween;
   an ankle block comprising a compressible foam material having a thickness of at least about one inch, said ankle block being positioned between said ankle plate and foot plate and occupying substantially all of said space formed between said foot plate and said ankle plate; and
   an attachment member secured to said ankle plate adapted to attach said prosthetic foot to a pylon or socket, said attachment member defining an attachment axis located posteriorly along a longitudinal center line at a point approximately two-thirds of the distance rearward along the length of said ankle plate;
   said foot plate, said ankle plate and said ankle block cooperating such that as said amputee walks on said foot, compression stress migrates substantially uniformly through said ankle block so as to provide substantially smooth rollover of said prosthetic foot.

2. The prosthetic foot of claim 1, wherein said ankle block comprises a single monolithic block of foam material having a thickness of between about one and three inches.

3. The prosthetic foot of claim 1, wherein said ankle block comprises a cellular polyurethane foam material having a density of between about 25–35 lbs/ft$^3$.

4. The prosthetic foot of claim 1, wherein said foot plate has a width roughly equal to that of a natural human foot.

5. The prosthetic foot of claim 4, wherein said ankle plate has a width roughly equal to that of a natural human foot.

6. A prosthetic foot, comprising:
   a substantially flat lower foot plate having a length and width approximately equal to that of a natural human foot being replaced, said foot plate having anterior and posterior ends and being constructed of a material capable of flexing along its length;
   a substantially flat upper ankle plate having a length shorter than said length of said foot plate, said ankle plate having anterior and posterior ends and being constructed of a material capable of flexing along its length, said foot plate and said ankle plate being disposed relative to one another so as to define a space therebetween;
   an ankle block of compressible foam material bonded to an upper surface of said foot plate and to a lower surface of said ankle plate, said ankle block having a length and width approximately equal to said ankle plate and occupying substantially the entire space between said ankle plate and said foot plate, said ankle plate being aligned with said ankle block and both being positioned rearward from a center of said foot plate; and
   an attachment member secured to said ankle plate adapted to attach said prosthetic foot to a pylon or socket, said attachment member defining an attachment axis located posteriorly along a longitudinal center line at a point approximately two-thirds of the distance rearward along the length of said ankle plate.

7. The prosthetic foot of claim 6, wherein said ankle block comprises a single monolithic block of a cellular polyurethane foam material having a density of between about 25–35 lbs/ft$^3$, said block of foam material having a width approximating the width of a natural human foot, a length that is shorter than that of a natural human foot and a thickness of between about one and three inches, said block of foam material having sufficient strength and resiliency such that it is capable of supporting substantially the entire weight of an amputee wearing said prosthetic foot while allowing substantially uniform migration of stress through said foam block in response to flexing of said flexible plate members.

8. A prosthetic foot, comprising:
   a substantially flat lower foot plate having a length and width approximately equal to that of a natural human foot being replaced, said foot plate having anterior and posterior ends and being constructed of a material capable of flexing along its length;

a substantially flat upper ankle plate having a length shorter than said length of said foot plate, said ankle plate having anterior and posterior ends and being constructed of a material capable of flexing along its length, said foot plate and said ankle plate being disposed relative to one another so as to define a space therebetween;

an ankle block of compressible foam material bonded to an upper surface of said foot plate and to a lower surface of said ankle plate, said ankle block having a length and width approximately equal to said ankle plate and occupying substantially the entire space between said ankle plate and said foot plate, said ankle plate being aligned with said ankle block and both being positioned rearward from a center of said foot plate; and an attachment member secured to said ankle plate adapted to attach said prosthetic foot to a pylon or socket, said attachment member defining an attachment axis located posteriorly along a longitudinal center line of said ankle plate and wherein said attachment member further comprises locating pins for aligning said prosthetic foot relative to said pylon or socket and for transmitting torsional forces from said prosthetic foot to said pylon or socket.

9. A prosthetic foot for replacing a natural human foot, said prosthetic foot comprising:

an elongated lower foot plate element having a length and width roughly equal to that of said natural human foot being replaced, said foot plate element having top and bottom surfaces and being formed of a resilient material having an area moment of inertia about a first axis that is substantially smaller than the area moment of inertia about a second axis perpendicular to said first axis such that said foot plate element is capable of flexing along its length in a first direction but not substantially in a second direction;

an elongated upper ankle plate element having a length shorter than said foot plate element, said upper ankle plate element having top and bottom surfaces and being formed of a resilient material having an area moment of inertia about a first axis that is substantially smaller than the area moment of inertia about a second axis perpendicular to said first axis such that said ankle plate element is capable of flexing along its length in a first direction, but not substantially in a second direction;

an elongated monolithic block of compressible foam material having a length and width roughly corresponding to that of said upper ankle plate element and a thickness of at least one inch, said monolithic block having a top surface and a bottom surface, the bottom surface of said monolithic block being secured to the top surface of said foot plate element such that they are substantially aligned along their respective axes of elongation, the top surface of said monolithic block being secured to the bottom surface of said ankle plate element such that they are substantially aligned along their respective axes of elongation; and an attachment member secured to said ankle plate element adapted to attach said prosthetic foot to a pylon or socket, said attachment member defining an attachment axis located posteriorly along a longitudinal center line at a point approximately two-thirds of the distance rearward along the length of said ankle plate element.

10. The prosthetic foot of claim 9 further comprising a sole cushion secured to said bottom surface of said foot plate element.

11. A prosthetic foot for providing resilient kinematic support to an amputee, said prosthetic foot comprising:

a lower foot plate element having a length from toe to heel roughly equal to that of a natural human foot being replaced, said foot plate element being monolithically formed of a resilient material having an area moment of inertia about a first axis that is substantially smaller than the area moment of inertia about a second axis perpendicular to said first axis such that said foot plate element is capable of flexing along its length in a fore-and-aft direction, but not substantially in a side-to-side direction, said foot plate element defining toe and heel portions of said prosthetic foot;

an upper ankle plate element having a length shorter than said foot plate element and being separately formed of a resilient material having an area moment of inertia about a first axis that is substantially smaller than the area moment of inertia about a second axis perpendicular to said first axis such that said ankle plate element is capable of flexing along its length in a fore-and-aft direction, but not substantially in a side-to-side direction;

an ankle block comprising a compressible foam material having a thickness of between about one and three inches, said ankle block being positioned between said ankle plate element and said foot plate element; and an attachment member secured to said ankle plate element adapted to attach said prosthetic foot to a pylon or socket, said attachment member defining an attachment axis located posteriorly along a longitudinal center line at a point approximately two-thirds of the distance rearward along the length of said ankle plate element;

said foot plate element, said ankle plate element and said ankle block cooperating such that as said amputee walks on said foot, compression stress migrates substantially uniformly through said ankle block such that substantially smooth rollover of said foot prosthesis is achieved.

12. The prosthetic foot of claim 11, wherein said ankle plate element and said foot plate element are of substantially the same width.

13. The prosthetic foot of claim 12, wherein said ankle block extends roughly said length of said ankle plate element.

14. The prosthetic foot of claim 13, wherein said ankle plate element extends roughly one-third the length of said foot plate element.

15. The prosthetic foot of claim 14, wherein said foot plate element comprises a resilient plate formed from a plurality of laminae embedded in a hardened flexible polymer material.

16. The prosthetic foot of claim 15, wherein said ankle plate element comprises a resilient plate formed from a plurality of laminae embedded in a hardened flexible polymer material.

17. The prosthetic foot of claim 13, wherein said ankle block comprises a monolithic block formed of a relatively compliant compressible foam material.

18. The prosthetic foot of claim 17, wherein said ankle block comprises a cellular polyurethane foam having a density of between about 25–35 lbs/ft$^3$.

19. The prosthetic foot of claim 13, wherein said foot plate element has a width roughly equal to that of a natural human foot.

20. The prosthetic foot of claim 19, wherein said ankle plate element has a width roughly equal to that of a natural human foot.

* * * * *

UNITED STATES PATENT AND TRADEMARK OFFICE
CERTIFICATE OF CORRECTION

PATENT NO. : 5,728,177
DATED : March 17, 1998
INVENTOR(S) : Van L. Phillips

It is certified that error appears in the above-identified patent and that said Letters Patent is hereby corrected as shown below:

On the Cover page of the Patent No. 5,728,177, issued March 17, 1998, please delete item number 73. This patent has not been assigned.

Signed and Sealed this

First Day of June, 1999

Attest:

Q. TODD DICKINSON

Attesting Officer

Acting Commissioner of Patents and Trademarks